United States Patent [19]

Greco

[11] Patent Number: 5,106,988

[45] Date of Patent: Apr. 21, 1992

[54] SILANES CONTAINING AT LEAST TWO OXAZOLIDINIC MOIETIES

[75] Inventor: Alberto Greco, Dresano, Italy

[73] Assignee: Enichem Synthesis S.p.A., Palermo, Italy

[21] Appl. No.: 510,448

[22] Filed: Apr. 18, 1990

[30] Foreign Application Priority Data

Apr. 18, 1989 [IT]  Italy ............................... 20189 A/89

[51] Int. Cl.$^5$ ................................................ C07F 7/10
[52] U.S. Cl. ..................................... 548/110; 544/222
[58] Field of Search ......................... 548/110; 544/222

[56] References Cited

FOREIGN PATENT DOCUMENTS 63-088189  4/1988  Japan .

OTHER PUBLICATIONS

Muelhaupt et al., Chemical Abstracts, vol. 108 (1988) 205739t.

Parrinello et al., Chemical Abstracts, vol. 114 (1990) 44237j.

*Primary Examiner*—Richard L. Raymond
*Attorney, Agent, or Firm*—Shea & Gould

[57] ABSTRACT

New silanes containing at least two oxazolidinic moieties can be defined by means of the general formula:

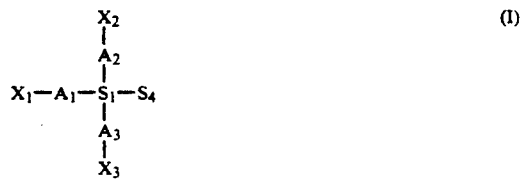

wherein $X_1$, $X_2$, $X_3$ and $X_4$ have the meaning as reported in the specification, and each one of $A_1$, $A_2$ and $A_3$ represents from 0 to a plurality of siloxane radicals —SiO— and are better defined in the text of the specification.

These compounds are useful as crosslinking agents for moisture-hardening systems based on polyisocyanates, of acrylate polymers and of polyepoxides in compositions for coatings, sealants and adhesive agents.

10 Claims, No Drawings

SILANES CONTAINING AT LEAST TWO OXAZOLIDINIC MOIETIES

The present invention relates to silanic compounds containing at least two oxazolidinic moieties, to the process for preparing them and to their use as crosslinking agents for moisture-hardening systems based on polyisocyanates, on acrylate polymers and on polyepoxides in compositions for coatings, sealants and adhesive agents.

In U.S. Pat. No. 3,743,626 the use is disclosed of some polyoxazolidines as hardening agents, under environmental conditions of moisture and temperature, for adhesives based on both aromatic and aliphatic polyisocyanates. As disclosed in U.S. Pat. No. 4,138,545, such polyoxazolidines can be obtained by means of the reaction of an oxazolidine (A):

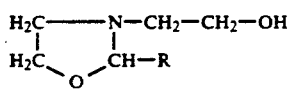

with lower alkyl esters of dicarboxy or polycarboxy acids, by operating under trans-esterification conditions; or by means of the reaction of an oxazolidine (B):

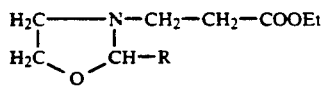

with a glycol or a polyol, still operating under conditions of transesterificaton. The oxazolidines (B) are obtained in their turn by means of the addition of aldehydes to an addition product obtained from ethanolamine and an alkyl acrylate.

Such reactions of transesterificaton require such catalysts as alkali-metal alkoxides or organometallic compounds (e.g., titanium alkoxides), which are not easily removed from the reaction medium and are harmful for the stability of polyisocyanates. Furthermore, drastic reaction conditions are required for the transesterification to proceed to completeness, with the obtained products being consequently damaged.

Belgian patent No. 865,893 discloses the use of some polyoxazolidines in sealant compositions based on polyisocyanates. As disclosed in Belgian patent No. 833,821, these polyoxazolidines can be obtained by means of the addition of oxazolidine (A) to polyisocyanates. These products suffer from the disadvantages deriving from the cost of polyisocyanates. Furthermore, owing to the formation of urethanes in their synthesis, these products have unacceptably high viscosity values, in particular when non-aliphatic diisocyanates, or polyisocyanates in general are used.

European patent application publ. No. 288,935 discloses the use of polyoxazolidines as crosslinking agents in putties based on polyisocyanates, crosslinking under environmental conditions of moisture. These polyoxazolidines use, as their starting products, bis(alkanolamines) (C):

The synthesis of such alkanolanies, carried out by starting from amines and ethylene oxide, is not very selective. Furthermore, the need exists for such reaction compounds to be separated from the reaction mass, under high-temperature, high-vacuum conditions. The distillation is required by the need for removing the tertiary amines (tri- and poly-alkanolamines) which, in case are introduced in polyisocyanate systems, reduce their useful life owing to phenomena of premature crosslinking, by a chemical (alkanols), as well as a catalytic (presence of tertiary nitrogen) way.

U.S. Pat. No. 4,296,225 discloses the incorporation of polyoxazolidines as latent crosslinking systems, in polyvinylic systems, in the preparation of polyvinylic emulsions. In this case, the oxazolidine is incorporated in the formulation as a hydroxyalkyloxazolidine methacrylate, or as a component in polyurethane paints with a high solids content. The principle is that of introducing the oxazolidinic moiety into the molecule of a polyacrylate. Such an introduction is made possible by means of the use of a vinyloxazolidine capable of copolymerizing to a various extent with the acrylic monomers. In any case, the oxazolidinic equivalent is not high and the polymers are either solids or liquids with an excessively high viscosity value, so that the compounds have to be dispersed in water, or must be dissolved in an organic solvent.

The purpose of the present invention is a novel class of compounds containing at least two oxazolidinic moieties in their molecule, which makes it possible the drawbacks of the prior art, as mentioned hereinabove, to be overcome.

In particular, according to the present invention a novel class of silanic compounds containing at least two oxazolidinic moieties in their molecule has been found, which can be prepared in a simple and economically advantageous way, and are used as crosslinking agents in moisture-hardening systems on the basis of polyisocyanates, acrylate polymers or polyepoxides, and which are characterized by a considerable thermal and photochemical stability chromatic stabily and very low viscosity.

In accordance therewith, and according to a first aspect thereof, the present invention relates to novel compounds which can be defined by means of the general formula:

wherein $A_1$, $A_2$ and $A_3$, which can be either equal to, or different from, one another, represent random sequences respectively of $m_1$, $m_2$ and $m_3$

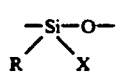

radicals and of $n_1$, $n_2$ and $n_3$

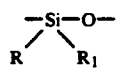

radicals, wherein $m_1$, $m_2$, $m_3$, $n_1$, $n_2$ and $n_3$ are integers comprised within the range of from 0 to 10 and at least two from the substituents X, $X_1$, $X_2$, $X_3$ and $X_4$ represent an N-alkyl-oxazolidinic radical (II):

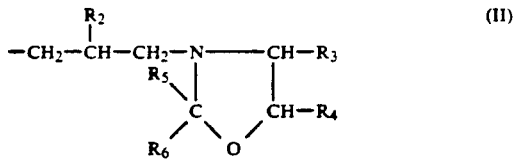

and the residual substituents, which can be either equal to, or different from, one another, represent, independently from one another: a hydrogen atom, a straight- or branched-chain alkyl radical containing from 1 to 6 carbon atoms, and which can be substituted with either organic or inorganic radicals inert towards the oxazolidinic structure (II), as well as towards the

bonds, and towards the isocyanate radicals —NCO, the epoxy or acrylic groups, and so forth, which are contained on the formulates the compounds of the instant invention are mainly destined to; an either straight or branched fluoroalkyl radical containing from 1 to 6 carbon atoms, an aryl or cycloalkyl radical, which can also be substituted on their ring with alkyl radicals, or with either organic or inorganic radicals which are inert in the hereinabove specified meaning, or a whatever pair of the $X_1$, $X_2$, $X_3$ and $X_4$ substituents, jointly taken, represent an oxygen bridge between the two silicon atoms they are bonded to, so as to originate a cyclic structure constituted by silicon and oxygen atoms in alternating sequence, and the residual two substituents, including the X substituent, retain their meaning as seen above;

R and $R_1$, which can be either equal to, or different from, each other, independently represent the hydrogen atom, a straight- or branched-chain alkyl radical containing from 1 to 6 carbon atoms, a cycloalkyl radical or an aryl radical, which can be also substituted on their ring with radicals inert towards the oxazolidinic structure; an either straight or branched fluoroalkyl radical containing from 1 to 6 carbon atoms;

$R_2$ represents the hydrogen atom or the methyl radical;

$R_3$ and $R_4$, which can be either equal to, or different from, each other, represent, independently from each other, the hydrogen atom, a straight- or branched-chain alkyl radical containing from 1 to 6 carbon atoms, or an aryl radical;

$R_5$ and $R_6$, which can be either equal to, or different from, each other, represent the hydrogen atom, a straight- or branched-chain alkyl radical containing from 1 to 6 carbon atoms, a cycloalkyl radical or an aryl radical.

For the sake of convenience of representation, the radicals $A_1$, $A_2$ and $A_3$ can be represented as:

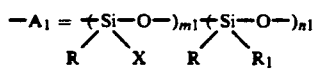

-continued

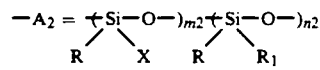

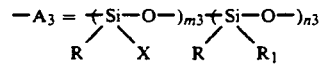

wherein $m_1$, $m_2$, $m_3$, $n_1$, $n_2$ and $n_3$, owing to as hereinabove said, are integers comprised within the range of from 0 to 10. The siloxanic chains should not absolutely be understood as a sequence of blocks, with blocks being constituted by an m number of

radicals with an n number of

radicals, in that the sequence of the two different siloxanic radicals is randomly distributed throughout the same chains.

By "radicals inert towards the oxazolidinic structure, the ≡Si—H bond and the isocyanate, epoxy and acryl groups", such radicals as $CH_3$, $C_2H_5$—$CF_3$, —CN, —$CH_2Cl$, and so forth are meant.

In accordance with the structural formula (I), the silanic compounds according to the present invention can be either straight (when at least two of the sums of $m_1+n_1$, $m_2+n_2$, $m_3+n_3$ are equal to zero), or branched (when at least two of the sums of $m_1+n_1$, $m_2+n_2$, $m_3+n_3$ are different from zero), or cyclic [when a whatever pair of the substituents $X_1$, $X_2$, $X_3$ and $X_4$ in the general formula (I), jointly taken, represent an oxygen bridge between the two silicon atoms they ar bonded to].

In the preferred form of practical embodiment of the present invention among the straight structures, $m_1$, $m_2$, $m_3$, $n_2$ and $n_3$ are equal to zero; $n_1=1$; R, $R_1$, $X_2$ and $X_3$ represent a methyl radical; $X_1$ and $X_4$ represent two N-alkyloxazolidinic moieties (II); the substituents $R_2$, $R_3$ and $R_4$ represent hydrogen atoms, and the substituents $R_5$ and $R_6$ represent, independently from each other, a straight- or branched-chain alkyl radical containing from 1 to 4 carbon atoms, or either one of $R_5$ and $R_6$ represents the hydrogen atoms and the other one represents an alkyl radical.

A particular example, non-limitative for the purposes of the present invention, of a compound according to the preferred form of practical embodiment among the straight structures, is bis-[(2-isopropyl-1,3-oxazolidin-3-yl)-propanyl]-tetramethyl-disiloxane (III)

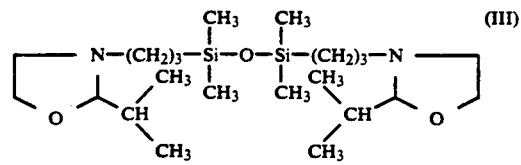

In case of branched silanic compounds, a preferred form of practical embodiment among the structures of general formula (I) is the one in which $m_1$, $m_2$ and $m_3$ are equal to zero; $n_1$, $n_2$ and $n_3$ are equal to 1; $X_4$, R and $R_1$ represent methyl radicals; $X_1$, $X_2$ and $X_3$ represent N-alkyl-oxazolidinic moieties (II); the substituents $R_2$, $R_3$ and $R_4$ represent hydrogen atoms; and the substituents $R_5$ and $R_6$ represent, independently from each other, a straight- or branched-chain alkyl radical containing from 1 to 4 carbon atoms, or either one of $R_5$ and $R_6$ represents the hydrogen atoms and the other one represents an alkyl radical.

A particular example, non-limitative for the purposes of the present invention, of a compound according to the preferred form of embodiment among the branched structures, is the compound having the structural formula (IV):

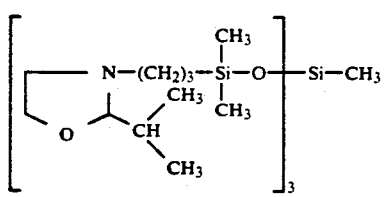

In case of cyclic silanes, falling within the scope of the general formula (I), in case a whatever pair of the substituents $X_1$, $X_2$, $X_3$ and $X_4$, jointly taken, represent an oxygen bridge between the two end silicon atoms they are bonded to, the structures corresponding to the general formula (V):

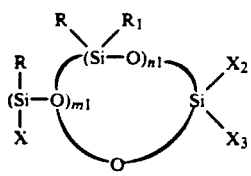

which fall within the scope of the general formula (I) in case $X_1$ and $X_4$, when jointly taken, represent an oxygen bridge between the two silicon atoms they are linked to, and $m_2$, $m_3$, and $n_2$, $n_3$ are equal to zero, constitute a preferred form of practical embodiment. We emphasize that the m

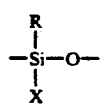

radicals and the n

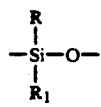

radicals have to be understood as being randomly distributed throughout the ring structure of formula (V).

Examples of compounds falling within the scope of the structural formula (V), non-limitative for the purposes of the instant invention, are bis-[(2-isopropyl-1,3-oxazolidin-3-yl)-propenyl]-tetramethylcyclotetrasiloxane (VI)

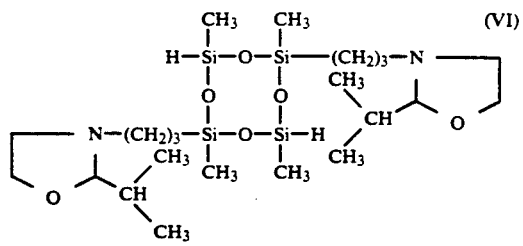

corresponding to the formula (V) for $m_1=2$ (owing to as above said, the two radicals are randomly distributed throughout the cycle); $n_1 1$, $R_1$ and $X_2=H$, R and $X_3$=methyl and X represents an N-alkyloxazolidinic radical according to formula (II); and tetra-[(2-isopropyl-1,3-oxazolidin-3-yl)-propanyl]-tetramethyl-cyclotetrasiloxane (VII), also falling within the scope of formula (V):

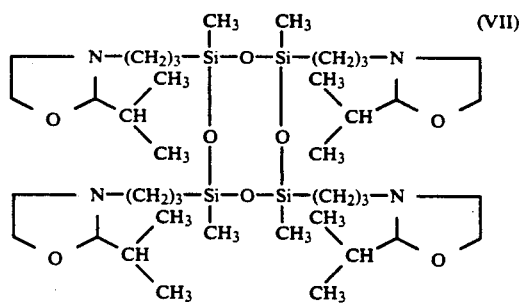

In the particular case of compounds falling within the scope of the structural formula (I) in which $m_1$, $m_2$, $m_3$, $n_1$, $n_2$ and $n_3$ are equal to zero and at least two radicals selected from the group consisting of $X_1$, $X_2$, $X_3$ and $X_4$ represent an oxazolidinic radical (II), the compounds are simple silanes of formula (VIII):

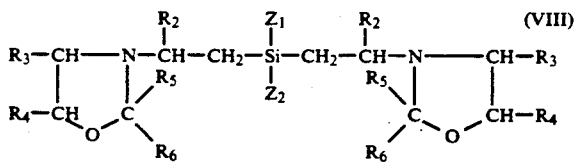

Among the structures having the general formula (VIII), bis-[(2-isopropyl-1,3-oxazolidin-3-yl)-propenyl]-diphenylsilane (IX):

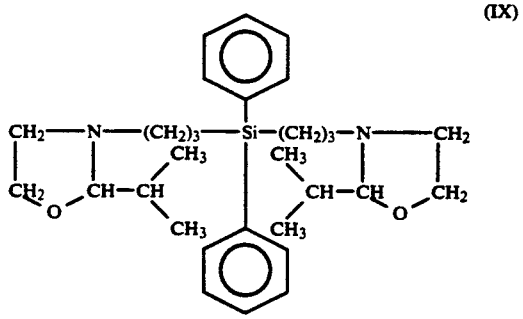

constitutes a preferred form of practical embodiment.

The siloxanic compounds according to the present invention are easily obtained by means of the reaction of a (meth)allyl-oxazolidine (X)

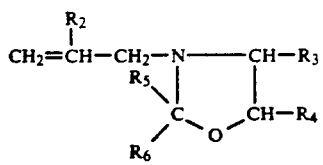

wherein the $R_2$, $R_3$, $R_4$, $R_5$ and $R_6$ substituent radicals have the same meaning as seen hereinabove, with a siloxanic compound having the general formula (XI)

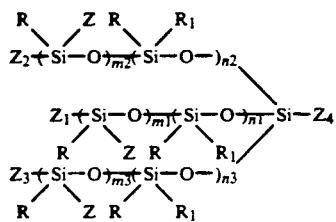

wherein $m_1$, $m_2$, $m_3$, $n_1$, $n_2$, $n_3$, R and $R_1$ have the same meaning as seen hereinabove, with Z, $Z_1$, $Z_2$, $Z_3$ and $Z_4$ respectively have the same meaning as of X, $X_1$, $X_2$, $X_3$ and $X_4$, with the obvious exception that they do not represent the N-alkyl-oxazolidinic radical (II), and that at least two thereof should represent the hydrogen atom.

The reaction, which involves the Si—H linkages of (XI) and can be schematically shown as follows:

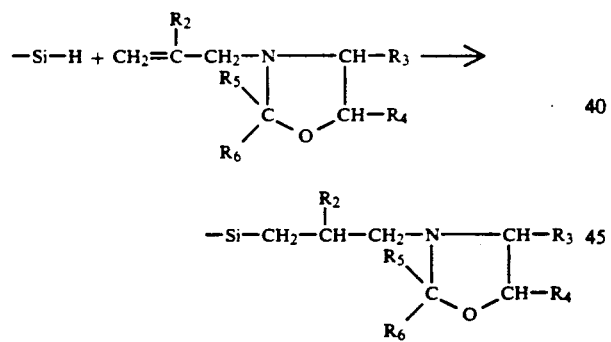

is carried out with stoichiometric, or lower-than-stoichiometric amounts of the reactants, wherein by "stoichiometric amount" a number of mols of (meth)-allyloxazolidine (X) has to be understood, which is equal to the number of Si—H bonds contained in the siloxanic compound (XI). In case amounts of (X) are used, which are smaller than the stoichiometric amount, the so obtained polysiolxanes will still contain Si—H linkages as in case of the above compound (VI).

In general, the reaction takes place very easily with heat development up to a vary high conversion rate, desirably in the presence of catalysts of temperatures comprised within the range of from 50° C. up to 150° C., and preferably comprised within the range of from 80° C. up to 120° C.

Reaction catalysts are palladium in metal state, rhodium, palladium complexes or complexes of still other transition metals, such as, e.g., hexachloroplatinic acid ($H_2PtCl_6$), or initiators of free-radical type, such as, e.g., azobisisobutyronitrile.

The amounts of catalyst are considerably different and strictly depending on the type of catalytic system adopted.

In case of catalysts of free-radical type, the amounts can be comprised within the range of from 0.01 up to 5%, and are preferably comprised within the range of from 1 to 5% by weight, relatively to the reactants.

On the contrary, in case of catalysts in metal form (Rh, Pd, Pt, and so forth), and of their compounds, the very low amounts of catalysts are used, and are generally comprised within the range of from 1 to 100 parts per million, as computed relatively to the reactants, and preferably comprised within the range of from 1 to 10 ppm.

In case acidic catalysts are used, such as, e.g., hexachloroplatinic acid, small amounts of a proton acceptor, such as, e.g., glycidol or trimethylorthoformate, should be added to the reaction medium in order to reduce the acidity of the system, to which the oxazolidinic molecule is very sensitive.

It is not necessary to operate under pressure; anyway, the reaction can be carried out in autoclave as well.

The reaction can be carried out in bulk or in the presence of inert solvents. The use of an inert solvent facilitates the removal and control of the rection heat.

By the term "inert solvents", all of those solvents are meant, which do not interact with Si—H function; the aliphatic and aromatic hydrocarbons, as well as the linear and cyclic ethers, and so forth, belong to this class of solvents.

If one operates in the absence of solvents, the control of the exothermic heat developed by the reaction can be easily carried out by portionwise adding the (meth)-allyl-oxazolidinic reactant (e.g., by adding it dropwise).

Independently on how the reaction is carried out, whether in the presence, or in the absence of solvents, the reaction is substantially complete within a time which nearly never is longer than 6 hours, and is generally comprised within the range of from 2 to 6 hours.

The progress of the reaction is monitored by spectroscopic way, by monitoring the decrease of the absorption band of ≡Si—H radical in the I.R. range, or of the allyl unsaturation of (meth)-allyl-oxazolidine. If the reaction is carried out in the presence of a solvent, this latter is removed after the end of the reaction by evaporation under vacuum.

The reaction yield is practically complete and, apart from the distillation of the solvent, the obtained products do not practically require any further purification.

The silanic product (I) are low-viscosity liquids; their viscosity is a function of the number of the oxazolidinic moieties contained in their molecule and of the length of possibly present siloxanic chains.

The (meth)-allyl-oxazolidines of general formula (X) can be prepared in their turn according to the same method as disclosed in a co-pending Italian patent application filed in the same Applicant's name. Such a method is reported here for the only purpose of integrating the specification of the invention according to the instant patent application.

In particular, a (meth)-allylamine (A) is reacted with an alkylene oxide (B) in order to yield a (meth)-allyl-alkanolamine (C):

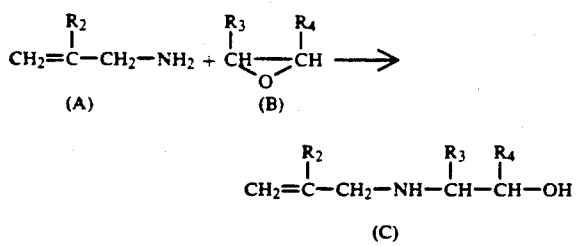

(C)

wherein $R_2$, $R_3$ and $R_4$ have the same meaning as seen hereinabove.

The reaction is exothermic and takes place easily at temperatures comprised within the range of from 0° C. to 120° C., by operating with a molar ratio of the (A) reactant to the (B) reactant comprised within the range of from 2 to 10.

The N-(meth)-allyl-alkanolamine (C) is the reacted with the aldehyde or ketone (D) in order to yield the (meth)-allyloxazolidine as the end product:

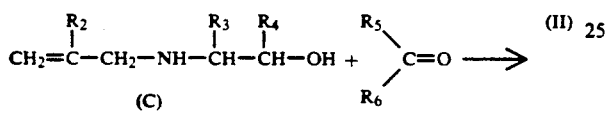

(II)

The reaction is suitably carried out at temperatures comprised within the range of from 20° C. to 100° C. without solvents, with the aldehyde or the ketone being refluxed in order to azeotropically remove water formed as the reaction byproduct.

The siloxanic compounds containing Si—H bonds of formula (XI) are well-known from patent literature and general technical literature.

The process for preparing the compounds (I) containing at least two oxazolidinic moieties, according to the instang invention, shows several advantages.

First of all, the values of yield and selectivity of the concerned reactions are high. Furthermore, the process is flexible, in that is makes it possible a variety of products to be obtained, which have a variable degree of functionality (number of oxazolidinic moieties).

Furthermore, the compounds (I) according to the present invention are compatible with the most common classes of organic polymers, with the advantage that they are liquids with rather low values of viscosity; moreover, said viscosity values can be easily controlled, in that, as said herinabov, they are directly depending on the number of the oxazolidinic moieties and on the length of the possibly present polysiloxanic chains (at least one from $m_1$, $m_2$, $m_3$, $n_1$, $n_2$ and $n_3$ is different from zero).

The length of the possibly present siloxanic chains (in case at least one from $m_1$, $m_2$, $m_3$, $n_1$, $n_2$ and $n_3$ is different from zero) and then, indirectly, the molecular weight of the compounds corresponding to the general formula (I) can be varied as desired, by causing the compounds (I) to react with polysiloxanes or with cyclopolysiloxanes in the presence of suitable catalysts.

So, e.g., the length of the chain of the siloxanic compound (III) can be extended by 4 —Si—O— units by reacting it with octamethyl-cyclotetrasiloxane (XII):

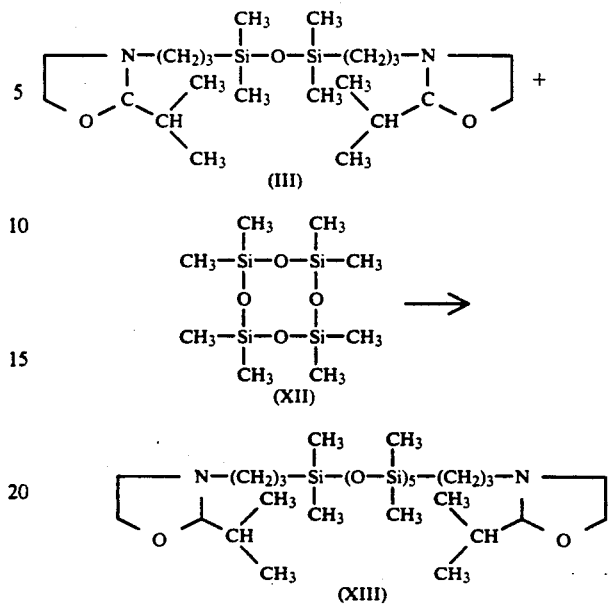

This type of reactions take place in the presence of alkaline catalysts, preferably KOH, NaOH and methylsilanolates, such as, e.g.:

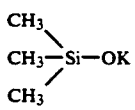

which cause the opening of the cycle of the cyclosiloxanic compounds and the cleavage of the chains of (III), with the higher-molecular-weight siloxanic compound being formed following a full series of intermediate rearrangement reactions.

Of course, also the process leading to the formation of the extended-chain compounds, like the above exemplified process in case of compound (XIII), fall within the scope of the instant invention.

The compounds (I) containing two or more oxazolidinic moieties according to the instant invention are latent crosslinking agents, in that in the presence of moisture, even of environmental humidity, they immediately undergo a hydrolysis, with the oxazolidinic ring being opened and polyalkanolamines being formed. Therefore, they are useful as crosslinking agents for polyisocyanates, polyepoxides and polyacrylates (Michael's addition), in coating, sealant and adhesive compositions. They are useful above all in combination with polyisocyanates in that, owing to their inherent features, they do not endanger their useful life, and therefore can be combined with said polyisocyanates in single-component systems, which are low-viscosity liquids under room conditions, are free from solvents and undergo crosslinking in the presence of environmental humidity. In these formulations, the low viscosity of compounds (I) is particularly beneficial.

The polyisocyanates which are useful for the purpose of the instant invention are: the diisocyanates available from the market, such as, e.g., hexamethylene-diisocyanate, isophorone-diisocyanate, p-toluene-diisocyanate, diphenylmethane-diisocyanate, and so forth; the polyisocyanates, whether available or not available from the market, which can be obtained by means of the reaction of the polyols (such as, e.g., trimethylolpropane), and monomer diisocyanates; the triisocyanates containing the isocyanurate ring, such as, e.g., the trimers of hexamethylene-diisocyanate or of isophorone-diisocyanate or of toluene-diisocyanate, having the structure:

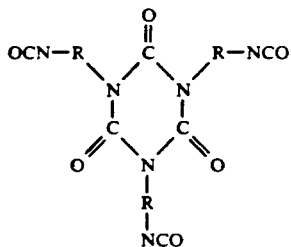

wherein R = —(CH₂)₆;

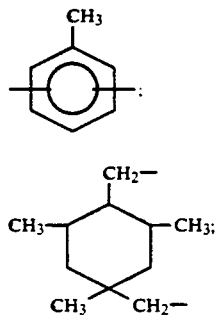

or those having polycondensed structures, of the types:

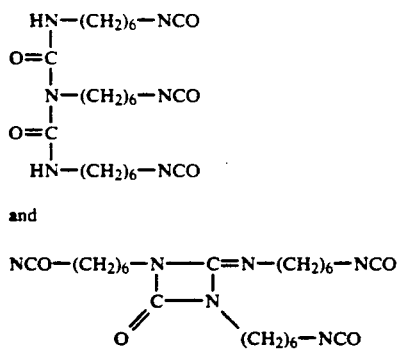

and

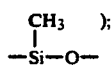

Furthermore, useful polyisocyanates for the hereinabove cited formulations are those polyisocyanates which can be obtained by starting from aliphatic and/or aromatic isocyanates and organic, either difunctional or polyfunctional polymers with a low molecular weight (i.e., with a molecular weight of the order of from 500 to 20,000), with hydroxy-capped chains. Among these, the polyethers, polyesters, polycarbonates, polybutadienes and some hybrid polymers, such as hydroxy-capped polycarbonate-copolyethers and polycarbonate-copolyesters, can be mentioned.

Such polyisocyanates are mixed with the compounds of formula (I) of the present invention in such a way, that to each oxazolidinic equivalent two equivalents of isocyanate radicals correspond in the polyisocyanate. Divergences from this stoichiometry are allowed, with the firmness of the crosslinked products being not excessively endangered, provided the compound (I) is present in an amount comprised within the range of from 30% less up to 20% in excess, relatively to the stoichiometric value.

The formulation containing the polyisocyanates and the compound (I) can be prepared at temperature values comprised within the range of from room temperature up to about 6020 C., and is facilitated by the perfect compatibility of the two concerned species with each other. To the formulation also catalysts can be added, which are suitable in order to speed-up the crosslinking process. Said catalysts are customarily selected from the group consisting of the metal soaps, and, in particular, the organometallic tin compounds, and of the organic acids, in particular p-toluene-sulfonic acid and naphthoic acid. Besides the catalysts further additives, such as organic or inorganic fillers, tixotropic agents flame-retarding agents, adhesion promoters, stabilizers, U.V.-absorbers can be added, according to the current common practice.

The so obtained formulations undergo crosslinking by the effect of environmental humidity, at a fairly good rate, yielding manufactured articles which are endowed with excellent characteristics, in particular as regards their heat resistance, their chemical resistance and their aging resistance, and with excellent characteristics of oxidation resistance.

The following examples are given for the only purpose of disclosing the invention in greater detail, and in no way should they be construed as being limitative of the purview of the same invention.

EXAMPLE NO. 1

Preparation of bis-oxazolidine 1-isopropyl-3-ally-1,3-oxazolidine ($X_a$) [72.6 g; 468.4 mmol], tetramethyldisiloxane [31.4 g; 41.0 ml; 234 mmol] and trimethyl-orthoformate [0.4 g] were charged to a large test tube of 200 ml of capacity, equipped with a magnetic-drive stirring means, and were reacted inside it under a dry-nitrogen blanketing atmosphere.

To the so obtained reaction mixture $H_2PtCl_6$ in isopropyl alcohol [0.5 mg of Pt; 10 ml ] was added and the resulting mixture was heated with stirring by means of an oil-bath up to the temperature of 110° C.: at this temperature a fast exothermic reaction started, with an inner temperature peak at 127° C.

The reaction was then allowed to proceed for a further 2 hours at 120° C.; at the end of this time, the absorption band of the function Si—H at 2120 cm$^{-1}$ of the I.R. spectrum had practically disappeared, like the absorption band typical for the allylic unsaturation at 2145 cm$^{-1}$.

The so obtained colourless oil was regarded as corresponding to the proposed structure, with a purity not lower than 95%.

$^1$H-N.M.R. (CDCl₃, TMS), signals at:
ppm 0.32 (12H, s, $$\underset{|}{\overset{CH_3}{\underset{-Si-O-}{|}}}\ );$$

ppm 0.75; 1.73; 2.82; [2H+2H+2H, m, respectively Si—CH₂—(α), Si—CH₂—CH₂— (β); Si—CH₂—CH₂—CH₂— (γ)];
ppm 1.22 (12H, m, 12H,

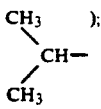

ppm 4.05 (2+1H, m,
ppm 2.55 and 3.4 (1+1H, m,
Elemental analysis: C 59.6%, H 11.0%; N 6.25%.

This compound was used in its as-produced-state for the successive uses (Tables, 1, 2, 3).

EXAMPLE NO. 2

Preparation of NCO-capped prepolymers and their formulation

Two NCO-capped polymers were respectively prepared by reacting at 75° two polymer-diols available from the market, i.e.: aliphatic-polycarbonate-diol (RAVECARB 107 by ENICHEM) (a liquid at room temperature, $t_g - 55°$ C.), and respectively, polytetrahydrofuran (a crystalline solid at room temperature, number average molecular weight = 2000), with isophorone-diisocyanate, NCO/OH ratio = 1.02.

The reaction was considered as complete when the —NCO function resulted to be consumed up to at least 95% of theoretical value.

To the so obtained NCO-capped prepolymers, the following values of number average molecular weight were respectively assigned:

$PM_n = 2300$ RAVECARB 107
$PM_n = 2450$ polytetrahydrofuran.

The following tests were subsequently carried out:

To 50 mmols of each one of the two polymers, respectively corresponding to 115 and 122.5 g, dibutyltin dilaurate (500 ppm), xylene (15 ml) and bis-(oxazolidine) of structure (III) were added in such proportions as reported in following Table 1. The so obtained formulates were homogenised (30 minutes, 50° C.) by stirring inside a sealed reactor, were degassed (1-2 hours at 50° C. under static vacuum), were spread in order to form a layer of 2 mm of thickness and were allowed to crosslink at +23° C. and 50% of relative humidity for 1 month. After crosslinking, the products showed the characteristics as reported in Table 1:

TABLE 1

| Test No. | Bis-oxazolidine (g) | Gel % | Tensile Strength N/mm² | Deformation (%) | Hardness (Shore A) |
|---|---|---|---|---|---|
| 1 | 10.5 | 90.2 | 14.4 | 1100 | 77 |
| 2 | 12.4 | 79.5 | 6.15 | 1200 | 64 |
| 3 | 13.3 | 78.5 | 4.5 | 1200 | 60 |
| 4 | 10.5 | 86.7 | 7.9 | 1300 | n.d. |

Further characteristics are reported hereinunder:

TABLE 2

| Test No. | Water Absorption (%) (*) | Oil Absorption (%) (**) |
|---|---|---|
| 1 | 1.65 | −1.1 |
| 2 | 0.8 | −1.5 |
| 3 | 1.0 | −1.6 |
| 4 | 2.36 | +20 |

Remarks:
(*) After being soaked in H₂O for 48 hours at 20° C.
(**) After being soaked in vaseline for 48 hours at +80° C.

All of the formulations showed to be stable over a storage time of up to 5 months at 50° C.

The 30-days-long exposure of the specimens to U.V. light (W—O—M) at the temperature of 40° C. on the samples 1, 2, 3, give the following results:

TABLE 3

| Test No. | Tensile Strength N/mm² | Deformation (%) | |
|---|---|---|---|
| 1 | 14.7 | 1200 | no yellowing |
| 2 | decays after 15 days | | no yellowing |
| 3 | decays after 55 days | | no yellowing |

EXAMPLE NO. 3

Preparation of tris-(oxazolidine) (IV)

Tris-(dimethylsiloxy)-methyl-silane (8.05 g, 9.4 ml, 0.0333 mol) was reacted with 1-isopropyl-3-allyl-1,3-oxazolidine (Xa) 15.5 g, 0.1 mol) in the presence of triethyl-orthoformate (0.2 ml) and a solution of H₂PtCl₆ in isopropanol (10 ml, 0.5 mg of Pt) for three hours at 110° C. At the end of this reaction time, the I.R. spectrum only showed the presence of traces of the absorption bands, respectively of Si—H at 2120 cm⁻¹ and of the double bond of N-allyl-oxazolidine at 1645 cm⁻¹.

The so obtained oil was then stripped at 90° C. for 2 hours under vacuum (0.5 torr) and left a residue of colourless oil corresponding to the designed structure (22.7 g, yield 96.6%).

Elemental analysis:
Found values: C 55.63%; H 10.5%; N 5.65% (IV),
Required values ($C_{34}H_{75}N_3O_6Si_4$ - M.W.=733) C55.66%; H 10.23%; N 5.73%.

EXAMPLE NO. 4

Preparation of bis-(oxazolidine) (VI)

Tetramethyl-orthosiloxane [24 g, 0.1 mol], N-allyl-oxazolidine (Xa) [31.5 g, 0.2 mol] were reacted in an analogous way to as disclosed in Example 3, in the presence of trimethyl-orthoformate (0.4 ml) and a solution of H₂PtCl₆ in isopropanol (10 ml, 0.5 mg of Pt). The I.R. spectrum of the resulting oil did not show any longer any traces of the presence of the double bond of allyl-oxazolidine at 1645 cm⁻¹, and the compound was assumed to be in compliance with the proposed structure.

The stripping of this oil at 90° C. under vacuum (0.5 torr) left a residue of 54.3 g (yield 97.8%).

Elemental analysis:
Found values: C 45.95%; H 9.5%; N 5.28% (VI),
Required values ($C_{20}H_{48}O_6Si_4$ - M.W.=524) C 45.80%; H 91.6%; N 5.34%,

EXAMPLE NO. 5

Formulation of the NCO-capped prepolymer with tris-(isoxazolidine) (IV)

The NCO-capped prepolymer based on aliphatic polycarbonate (RAVECARB 107) of Example No. 2 [50 mmol, 115 g] was added to trisoxazolidine (IV) of Example No. 3 (11.6 g), xylene (15 ml) and dibutyltin dilaurate (500 ppm).

After being homogenized by means of a mechanical stirrer and degassed, the resulting polymer was spread in order to form a layer of 2 mm of thickness, and was crosslinked under the same conditions as disclosed in Example No. 2.

After crosslinking, it displayed the following characteristics

| | |
|---|---|
| • Gel % | 90 |
| • Hardness (Shore A) | 70 |
| • Tensile strength (N/cm$^2$) | 20.2 |
| • Deformation (%) | 1200 |
| • H$_2$O absorption (%) | 1.0 (48 hrs in H$_2$O at 20° C.) |
| • Oil absorption (%) | −1.8 (48 hrs in vaseline at +80° C.) |

What is claimed is:

1. Silanic compounds containing at least two oxazolidinic moieties having the formula:

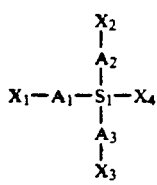

(I)

wherein A$_1$, A$_2$ and A$_3$, which can be the same or different from one another, represent random sequences respectively of m$_1$, m$_2$ and m$_3$ of the

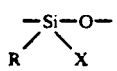

radicals and of n$_1$, n$_2$ and n$_3$ of the

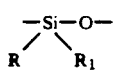

radicals wherein m$_1$, m$_2$, m$_3$, n$_1$, n$_2$, n$_3$ are integers comprised within the range of from 0 to 10; at least two of X, X$_1$, X$_2$, X$_3$ and X$_4$ represent an N-alkyl-oxazolidinic radical (II) having the formula

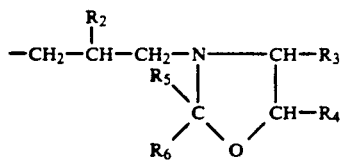

(II)

and the remainder of X, X$_1$, X$_2$, X$_3$ and X$_4$ which can be the same or different from one another, represent a hydrogen atom, a straight- or branched-chain, substituted or unsubstituted alkyl radical containing from 1 to 6 carbon atoms, straight chain or branched, substituted or unsubstituted aryl or cycloalkyl radical, which are inert towards the oxazolidinic radical, Si—H bonds, isocyanate radicals of the formula —NCO and, the epoxy and acrylate groups; or two of the substituents X$_1$, X$_2$, X$_3$ and X$_4$ taken together represent an oxygen bridge between the two silicon atoms they are bonded to forming a cyclic structure containing silicon and oxygen atoms in alternating sequence; and wherein R and R$_1$, which can be the same or different from each other, are selected from the same groups as defined above for X, X$_1$, X$_2$, X$_3$ and X$_4$; R$_2$ represents a hydrogen atom or a methyl radical; R$_3$ and R$_4$, which can be the same or different from each other represent a hydrogen atom, a straight- or branched-chain alkyl radical containing from 1 to 6 carbon atoms, or an aryl radical; R$_5$ and R$_6$, which can be the same or different from each other, represent a hydrogen atom, a straight- or branched-chain alkyl radical containing from 1 to 6 carbon atoms, a cycloalkyl radical or an aryl radical.

2. Silanic compounds according to claim 1, characterized in that the radicals A$_1$, A$_2$, A$_3$ can be represented as:

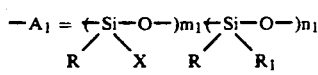

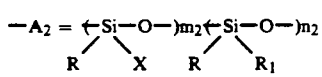

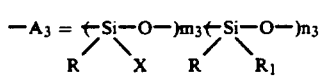

wherein m$_1$, m$_2$, m$_3$, n$_1$, n$_2$, n$_3$, R, X and R$_1$ have the same meaning as reported in claim 1, and wherein the different m$_1$ and n$_1$, m$_2$ and n$_2$, m$_3$ and n$_3$ siloxane radicals are randomly distributed throughout the siloxane chains respectively indicated by A$_1$, A$_2$ and A$_3$, such as to yield a statistical sequence.

3. Silanic compounds according to claim 1, characterized in that the substituents are selected from the group containing the radicals —CH$_3$, —C$_2$H$_5$, —CF$_3$, —CN, —CH$_2$Cl.

4. Silanic compound according to claim 1, constituted by bis--[(2-isopropyl-1,3-oxazolidin-3-yl)-propanyl]-methyl-disiloxane (III)

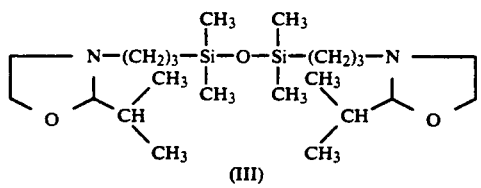

(III)

5. Silanic compound according to claim 1, characterized in that the compound (I) is the polysiloxane having the branched structure (IV):

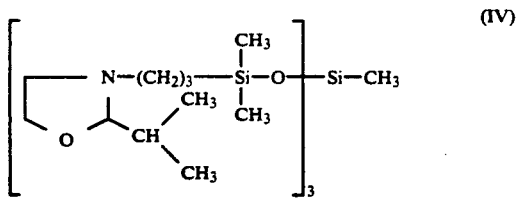

(IV)

6. Silanic compounds according to claim 1, characterized in that they have a cyclic structure (V):

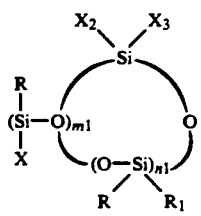

7. Silanic compound according to claim 5, constituted by bis-[(2-isopropyl-1,3-oxazolidin-3-yl)-propanyl]- tetramethylcyclotetrasiloxane (VI)

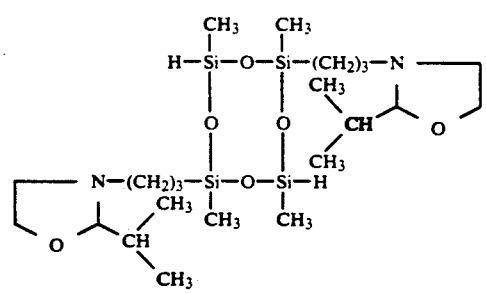
8. Silanic compound according to claim 5, constituted by tetra-[(2-isopropyl-1,3-oxazolidin-3-yl)-propanyl]-tetramethyl-cyclotetrasiloxane (VII):
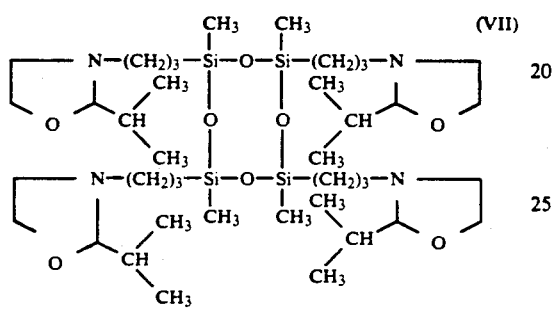
9. Silanic compound according to claim 1, having the structural formula (VIII):
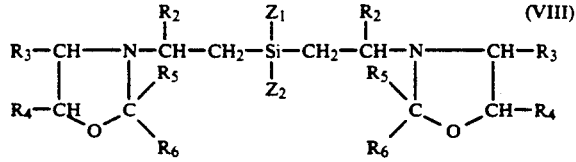
10. Silanic compound according to claim 9, constituted by bis-[(2-isopropyl-1,3-oxazolidin-3-yl)-propanyl]-diphenylsilane (IX):
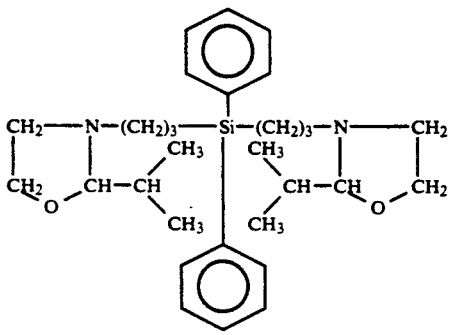
* * * * *